United States Patent [19]
Crainich

[11] Patent Number: 5,222,975
[45] Date of Patent: Jun. 29, 1993

[54] SURGICAL STAPLES

[76] Inventor: Lawrence Crainich, P.O. Box 996, Charlestown, N.H. 03603

[21] Appl. No.: 912,306

[22] Filed: Jul. 13, 1992

[51] Int. Cl.⁵ .............................................. A61B 17/00
[52] U.S. Cl. .................................... 606/219; 227/901; 411/457
[58] Field of Search .................. 606/219; 227/901, 19; 411/457

[56] References Cited

U.S. PATENT DOCUMENTS

| 4,014,492 | 3/1977 | Rothfuss | 606/219 |
| 4,399,810 | 8/1983 | Samuels et al. | 606/219 |
| 4,407,286 | 10/1983 | Noiles | 411/457 |
| 4,607,638 | 8/1986 | Crainich | 606/219 |
| 4,669,647 | 6/1987 | Storace | 606/219 |
| 4,802,478 | 2/1989 | Powell | 606/219 |

Primary Examiner—Stephen C. Pellegrino
Assistant Examiner—Gary Jackson
Attorney, Agent, or Firm—Bachman & LaPointe

[57] ABSTRACT

Surgical staples with an improved configuration including a humpbacked configuration providing significant advantages for stacking and staple rotation.

9 Claims, 2 Drawing Sheets

SURGICAL STAPLES

BACKGROUND OF THE INVENTION

Surgical staples to close incisions or wounds in body tissue are well known in the art, as are surgical stapling apparatus for applying the staples, for example, see U.S. Pat. Nos. 4,014,492, 4,043,504, 4,265,226, 4,375,866, 4,399,810, 4,407,286 and 4,607,638.

The surgical staples have a U-shaped configuration with an elongated or broad base portion, relatively square or slightly curved corners and two relatively shorter legs perpendicular to the base connected thereto at the corners and terminating at the other end in a sharpened, skin-piercing point. The staples are typically applied by a stapling apparatus wherein a group of same are held in the apparatus and advanced toward an anvil by a staple pusher having an end with a generally U-shaped recess. The base of the U-shaped recess in the staple pusher is broader than the anvil, but not as broad as the base of the U-shaped staple. When the staple reaches the anvil, the staple pusher causes the staple to bend or be deformed around the anvil into an open-sided, substantially O-shaped configuration by bending the staple at two points along the elongated base portion. This procedure can be referred to as forming the staple. As this is taking place the sharpened points of the staple enter the tissue on opposite sides of the incision or wound and draw the tissue together. When the staple has been fully formed, the staple pusher is retracted and the stapler is removed by sliding the anvil out from within the staple. The staple remains within the tissue to hold the tissue together during healing and is removed after healing by a staple remover.

It is desirable to provide an improved surgical staple configuration which permits easy feeding and orientation of the staple and promotes ease of forming with the tissue space.

Accordingly, it is a principal object of the present invention to provide an improved surgical staple configuration.

It is a further object of the present invention to provide improved surgical staple configurations which enable easy feeding and orientation and which promote ease of forming within the tissue space.

Further objects and advantages of the present invention will appear hereinafter.

SUMMARY OF THE INVENTION

In accordance with the present invention it has now been found that the foregoing objects and advantages may be readily obtained.

The surgical staple of the present invention has a generally U-shaped configuration with an elongated base and two legs substantially but not necessarily exactly perpendicular to the base and connected thereto at one end by first transition portions and terminating at the other end in sharpened points, with the base extending between the first transition portions. The staple is deformed in use into an open-sided, substantially U-shaped configuration bent at least at two points along the elongated base. The base is provided with a humpbacked configuration with at least one humpbacked portion thereof, wherein the humpbacked portion extends in a direction opposed to the legs, i.e., in a direction away from the center of the U-shaped configuration.

The base includes second transition portions extending along the base and inwardly of the first transition portions. The staple may be deformed in use (1) at the second transition portions and also (2) at the first transition portions.

The second transition portions are on the base and spaced inwardly from the first transition portions. In an alternative embodiment, the staple is deformed in use (1) at points between the first transition portions and second transition portions and also (2) at the first transition portions, to form a deformed staple having a humpbacked region therein corresponding to the humpbacked portion.

In a further embodiment, the legs extend inwardly towards each other and the base includes an outwardly extending region which extends between the first and second transition portions in a direction opposed to the legs, i.e., in a direction away from the center of the U-shaped configuration. This staple is deformed in use at the second transition portions to form a deformed staple having an outwardly extending region corresponding to the outwardly extending region of the base.

In a still further embodiment, the base includes an inwardly extending region which extends between the first and second transition portions, i.e., towards the center of the U-shaped configuration, in a direction towards the legs, wherein the staple is deformed in use at the second transition portions to form a deformed staple having an inwardly extending region corresponding to the inwardly extending region of the base.

Further features of the present invention will appear hereinbelow.

BRIEF DESCRIPTION OF THE DRAWINGS

The present invention will be more readily understandable from a consideration of the following illustrative drawings, in which.

DETAILED DESCRIPTION OF PREFERRED EMBODIMENTS

The staple of the present invention includes a base portion with a humpbacked configuration, i.e., with a base portion including at least one protruding portion that protrudes away from the center of the U-shaped staple configuration. This staple configuration provides unrestricted feeding without the need for close toleranced staple tracks. Also, the staples can be stacked without angularity and thereby stack more staples in a given space. The hump on the backspan or base portion facilitates a 90° rotation of the staple in front of the stack for applying the staple with an apparatus. One simply holds the staple at the hump portion and pushes on the adjacent surfaces for rotation thereof. In addition, the present staple configuration is highly useful for laparoscopic endoscopic surgery wherein the size of the stapling device is limited by the smaller puncture wound into the abdominal wall for insertion of a round cannula. Also, the humpbacked configuration is conducive to the round configuration of the stapling device that will house, orient and fire the staple.

Figure 1:
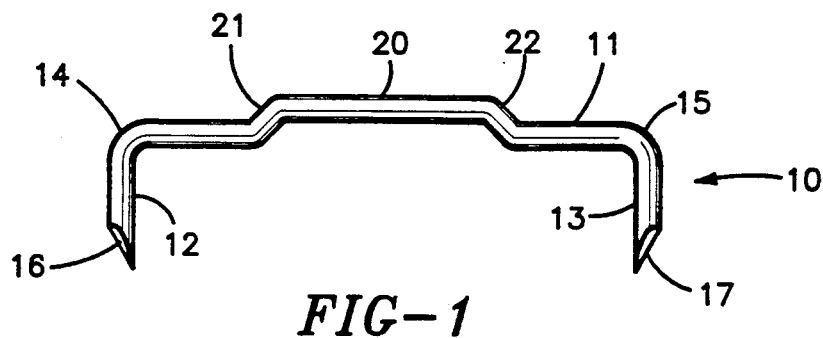
FIG. 1 is a side view of a staple of the present invention.
Figure 2:
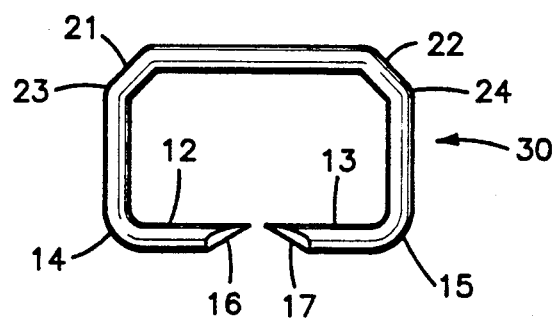
FIG. 2 is the staple of FIG. 1 after the forming procedure.

Referring to the drawings, FIGS. 1 and 2 are side views of a surgical staple of the present invention, before and after forming. As can be seen from FIG. 1 (before forming) the staple has a U-shaped configuration and a substantially round cross-section, i.e., the staple is formed from wire, as for example 316L surgical stainless steel, titanium or other materials conducive to surgical stapling. The staples may be made from shaped wire such as oval, flatted round, "D" shaped, rectangular or square but not limited to the aforementioned configurations.

The staple 10 of FIG. 1 has an elongated base portion 11 and two legs 12 and 13 substantially perpendicular with respect to the base portion. The legs are integral with the base portion and are connected thereto by first transition portions 14 and 15 which are slightly curved in shape. The legs terminate at the ends opposed to the transition portions in sharpened points 16 and 17. As can be clearly seen in FIG. 1, the legs are substantially shorter than the base portion so that the combined length of both legs can be shorter than the length of the base portion or longer to overlap when formed, although the present invention should not be limited to any particular leg or base length.

As seen in FIG. 1, base 11 has a humpbacked configuration and includes at least one humpbacked portion 20 which extends outwardly in a direction opposed to legs 12 and 13 and away from the center of the U-shaped configuration. Thus, base 11 includes second transition portions 21 and 22 extending along base 11 inwardly of first transition portions 14 and 15 and connecting the humpbacked portion 20 with base 11, wherein the second transition portions extend to the humpbacked portion.

In the forming operation, the staple is deformed in use into the configuration 30 shown in FIG. 2 into an open-sided, substantially 0-shaped configuration bent at two points 23, 24 along the elongated base at the second transition points 21 and 22. In addition, staple 10 is also deformed in use as shown in FIG. 2 by bending at the first transition points 14 and 15. As can be seen in FIG. 2, legs 12 and 13 are thereby bent inwardly so that sharpened points 16 and 17 face but do not touch one another or can overlap if desired and that the bent points correspond to the transition portions.

Figure 3:
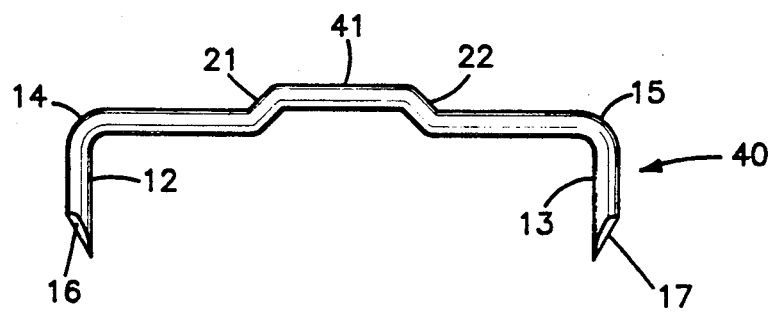
FIGS. 3-8 are side views similar to FIGS. 1 and 2 showing alternate embodiments.
Figure 4:
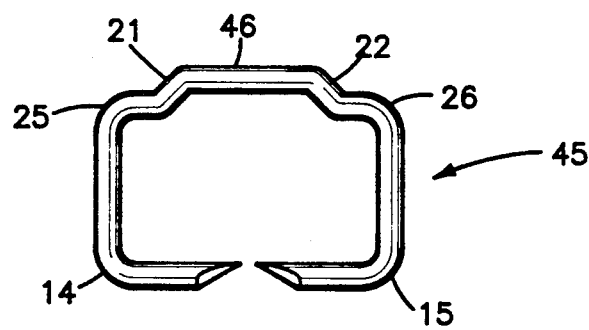

In accordance with the embodiment of FIGS. 3 and 4, the humpbacked portion 41 is shorter than humpbacked portion 20 in FIG. 1, whereby in use the staple 40 is deformed (1) at points 25, 26 between the first transition portions 14 and 15 and second transition portions 21 and 22 as well as (2) at the first transition portions 14 and 15 to form a deformed staple 45 shown in FIG. 4 having a humpbacked region 46 therein corresponding to humpbacked portion 41.

Thus, as can be seen the present invention contemplates within its scope different sizes for the humpbacked portion.

Figure 5:
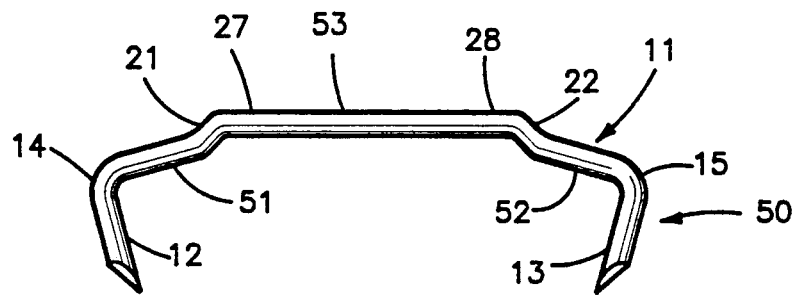
Figure 6:
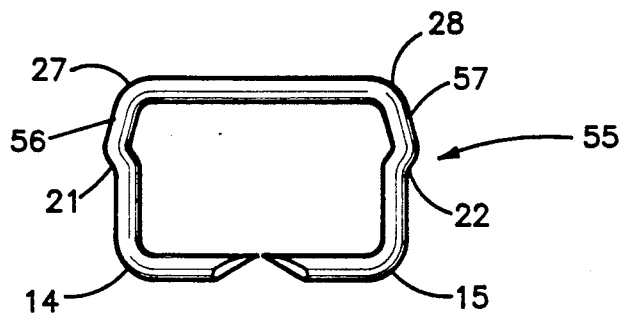

In accordance with the embodiment of FIGS. 5 and 6, staple 50 is provided with legs 12 and 13 which extend inwardly towards each other, i.e., towards the center of the U-shaped configuration and humpbacked region 53. Thus, the second transition portions 21 and 22 extend inwardly of the first transition portions 14 and 15 with base 11 having outwardly extending regions 51 and 52 extending between the first and second transition portions in a direction opposed to legs 12 and 13, i.e., extending outwardly in a direction opposed to the center of the U-shaped configuration.

The deformed staple 55 formed from staple 50 is deformed at the first transition portions and inwardly of the second transition portions at 27, 28 to form outwardly extending regions 56 and 57 corresponding to the outwardly extending regions 51 and 52 of the base.

Figure 7:
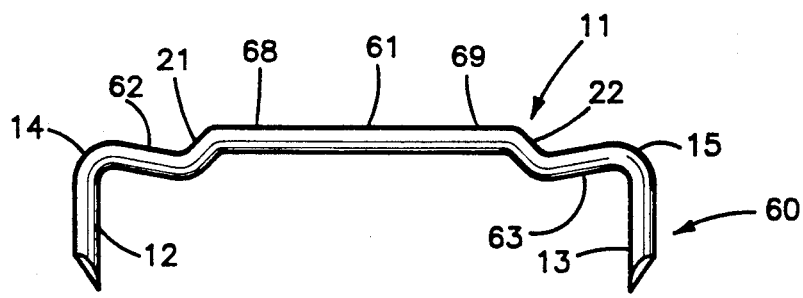
Figure 8:
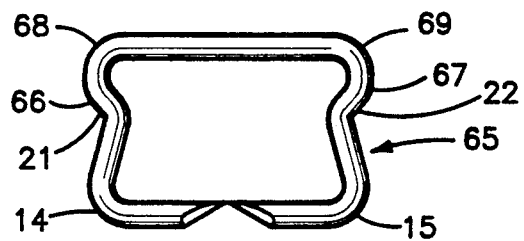

In accordance with the embodiment of FIGS. 7 and 8, staple 60 is also provided with legs 12 and 13 and humpbacked region 61 plus first and second transition portions as with the other embodiments, but base 11 has inwardly extending regions 62 and 63 which extend between the first and second transition portions, i.e., which extend towards the center of the U-shaped configuration. In use, staple 60 is deformed into the configuration of staple 65 shown in FIG. 8 wherein the staple is deformed at the first transition portions and inwardly of the second transition portions at 68, 69 to form a deformed staple having inwardly extending regions 66 and 67 corresponding to the inwardly extending regions 62 and 63 of the base.

The staples of the present invention offer considerable advantages as aforesaid. Thus, the staple of FIGS. 1 and 2 offer feed and orientation advantages and a deeper box length within the same staple length, particularly within the confines of a round apparatus inserted into a cannula. The staple of FIGS. 3 and 4 and FIGS. 7 and 8 offer feed and orientation advantages. The staple of FIGS. 5 and 6 offer feed and orientation advantages plus ease of forming.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A surgical staple having in the undeformed state a U-shaped configuration with an elongated base having a cross-section and two legs substantially perpendicular to said base and connected thereto at one end by first transition portions and terminating at the other end in sharpened points, with said base extending between the first transition portions, said staple in the deformed state having an open-sided, substantially O-shaped configuration bent at least at two points along said elongated base, wherein in the undeformed state said base has a humpbacked configuration with at least one humpbacked portion with the humpbacked portion extending outwardly in a direction opposed to said legs and with the entire cross-section of the elongated base extending outwardly out of the plane of the elongated base at the humpbacked portion, wherein the base includes second transition portions extending along the base inwardly of the first transition portions and extending to the humpbacked portion.

2. Staple according to claim 1 wherein in the deformed state the staple is bent at the first and second transition portions.

3. Staple according to claim 4 wherein in the undeformed state said legs extend towards each other.

4. Staple according to claim 3 wherein in the undeformed state the base has an outwardly extending region which extends between the first and second transition portions in a direction opposed to the legs, and in the deformed state said staple having an outwardly extending region corresponding to the outwardly extending region of the base in the undeformed state.

5. Staple according to claim 2 wherein in the undeformed state the base has an inwardly extending region which extends between the first and second transition portions, and in the deformed state said staple having an inwardly extending region corresponding to the inwardly extending region of the base in the undeformed state.

6. Staple according to claim 1 wherein in the deformed state the staple is bent at points between the first and second transition portions and at the first transition portions, to form a deformed staple having a humpbacked region therein corresponding to said humpbacked portion.

7. Staple according to claim 1 wherein in the deformed state the staple is bent (1) at points inwardly of the second transition portions and (2) at the first transition portions.

8. Staple according to claim 1 wherein in the undeformed state the humpbacked portion is located intermediate said first transition portions.

9. Staple according to claim 8 wherein in the undeformed state said humpbacked portion is a single, continuous humpbacked portion.

* * * * *

UNITED STATES PATENT AND TRADEMARK OFFICE
CERTIFICATE OF CORRECTION

PATENT NO. : 5,222,975

DATED : June 29, 1993

INVENTOR(S) : Lawrence Crainich

It is certified that error appears in the above-identified patent and that said Letters Patent is hereby corrected as shown below:

In Column 4, claim 3, line 58, "claim 4" should read
--claim 2--.

Signed and Sealed this

Eighth Day of February, 1994

*Attest:*

BRUCE LEHMAN

*Attesting Officer*     *Commissioner of Patents and Trademarks*